(12) United States Patent
Mante et al.

(10) Patent No.: US 8,614,263 B2
(45) Date of Patent: Dec. 24, 2013

(54) NON-BIODEGRADABLE ENDODONTIC SEALANT COMPOSITION

(75) Inventors: Francis K. Mante, Villanova, PA (US); Miri Kim, Seoul (KR); Syngcuk Kim, Broomall, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 132 days.

(21) Appl. No.: 12/701,924

(22) Filed: Feb. 8, 2010

(65) Prior Publication Data

US 2010/0203482 A1 Aug. 12, 2010

Related U.S. Application Data

(60) Provisional application No. 61/150,498, filed on Feb. 6, 2009.

(51) Int. Cl.
*A61K 6/08* (2006.01)

(52) U.S. Cl.
USPC .......................................... 523/115; 523/116

(58) Field of Classification Search
USPC .................................................. 523/115, 116
See application file for complete search history.

(56) References Cited

U.S. PATENT DOCUMENTS

| | | | |
|---|---|---|---|
| 3,575,946 A | 4/1971 | Chromecek et al. | |
| 3,925,895 A | 12/1975 | Kliment et al. | |
| 4,103,002 A * | 7/1978 | Hench et al. | 428/155 |
| 4,159,358 A * | 6/1979 | Hench et al. | 427/318 |
| 4,171,544 A * | 10/1979 | Hench et al. | 623/23.62 |
| 4,189,325 A * | 2/1980 | Barrett et al. | 106/35 |
| 4,234,972 A * | 11/1980 | Hench et al. | 623/23.57 |
| 4,478,904 A * | 10/1984 | Ducheyne et al. | 428/294.4 |
| 4,544,359 A * | 10/1985 | Waknine | 522/14 |
| 4,547,531 A * | 10/1985 | Waknine | 523/116 |
| 4,775,646 A * | 10/1988 | Hench et al. | 501/2 |
| 4,851,046 A * | 7/1989 | Low et al. | 106/35 |
| 5,074,916 A * | 12/1991 | Hench et al. | 106/35 |
| 5,415,547 A | 5/1995 | Torabinejad et al. | |
| 5,810,595 A * | 9/1998 | Mallow | 433/228.1 |
| 6,051,247 A * | 4/2000 | Hench et al. | 424/423 |
| 6,787,584 B2 * | 9/2004 | Jia et al. | 523/115 |
| 7,275,933 B2 * | 10/2007 | Jia et al. | 433/228.1 |
| 7,331,789 B2 * | 2/2008 | Karmaker et al. | 433/220 |
| 2002/0120033 A1 * | 8/2002 | Jia et al. | 523/115 |

FOREIGN PATENT DOCUMENTS

WO WO 2004103425 A1 * 12/2004

OTHER PUBLICATIONS

Cycotoxicity evaluation of a new radiopaque resin additive—triphenyl bismuth, H.R. Rawls et al. Den Mater 8:54-59, Jan. 1992.*
Yosef Nahmias et al., "Mineral Trioxide Aggregate (MTA) and its Uses", The First Electronic Endodontic Magazine 2007, http://www/endoweb.com/dentist/nah_ber1.htm.
Jin-Seon Song et al., "Chemical Analysis of Powder and Set Forms of Portland Cement, Gray ProRoot MTA, White ProRoot MTA, and Gray MTA-Angelus", Oral Surg Oral Med Oral Pathol Oral Radiol Endod., (2006), vol. 102, No. 6, pp. 809-815.
U. I. Walther et al., "Antioxidative Vitamins Decrease Cytotoxicity of HEMA and TEGDMA in Cultured Cell Lines", Archives of Oral Biology (2004), vol. 49, pp. 125-131.

* cited by examiner

*Primary Examiner* — James J Seidleck
*Assistant Examiner* — Peter A Salamon
(74) *Attorney, Agent, or Firm* — RatnerPrestia

(57) ABSTRACT

A non-biodegradable endodontic sealant composition comprises the reaction product of a first paste and a second paste. Either paste or both pastes include one or more of: unmodified HEMA and bioglass. The first paste includes a first polymerizing agent and the second paste includes a second polymerizing agent. A method for making the composition comprises preparing the first paste and second paste and combining the pastes under conditions to achieve a polymerization reaction initiated by a reaction between the polymerizing agents. The combining step is performed under conditions for achieving a setting time that is in a range of about 1 minute to about 1 hour. A method for treating humans having a voided region into which no re-growth will occur comprises administering the composition to the affected area, preferably to an area where tissue, tooth, or bone are not intended to re-grow.

24 Claims, No Drawings

NON-BIODEGRADABLE ENDODONTIC SEALANT COMPOSITION

CROSS REFERENCE TO RELATED APPLICATION

This application claims priority of U.S. Provisional Patent Application Ser. No. 61/150,498 filed Feb. 6, 2009, which is incorporated by reference herein in its entirety.

FIELD OF THE INVENTION

The present invention pertains to endodontic sealant compositions and particularly to non-biodegradable endodontic sealant compositions.

BACKGROUND OF THE INVENTION

Endodontic sealants are used to seal portions of dental roots and are often used for root canal treatment. In order to be effective, endodontic sealants should be non-toxic to the patient and biocompatible with surrounding tissue, tooth, and bone. Many clinical applications of endodontic sealant exist in endodontic and pedodontic practice. Uses of endodontic sealant for tooth root treatment include, for example, sealing of perforations, furcation repair, pulp capping, apexification, repairing root that is damaged during a root canal procedure, and treating root resorption. Endodontic sealants may also be used as retrograde filling materials or pulpotomy agents.

Biodegradable dental compositions are often used as bone replacement materials, such as bone grafts, because the compositions degrade and allow new bone or other tissue to substantially replace the composition. For example, U.S. Pat. No. 6,787,584 discloses a degradable dental composition which is intended to interact with surrounding tissues to promote regrowth of tissue and bone. For endodontic sealants, however, biodegradability is a disadvantage. Rather, one of the main purposes of endodontic sealants is to provide a lasting seal which remains in place and is not re-absorbed by the body. Non-biodegradability ensures that the affected area remains sealed off from surrounding tissue, tooth, and bone. One of the advantages of non-biodegradability, for example, is that bacteria and other infectious organisms are prevented from migrating into the root canal cavity or from the root canal into bone.

Efforts have been made to provide endodontic sealants which are non-biodegradable. For example, ProRoot® MTA (Mineral Trioxide Aggregate), sold by Dentsply, is used as a non-biodegradable endodontic sealant. In its clinical application, the MTA powder is mixed with water to provide a grainy mixture, and is then delivered and gently packed into the desired area. MTA is biocompatible and provides an effective sealant for tooth roots. However, MTA requires moisture to solidify or set, with setting times varying from approximately 3.5 hours to approximately 5 hours. Due to the long setting time, post-operative bleeding may cause portions of the sealant to be lost from the site of application. Also, in applications where a moist cotton pellet is placed on top of the MTA to ensure proper setting, a second treatment is required to remove the pellet, thus causing discomfort and inconvenience for the patient. Accordingly, it is desirable to provide an endodontic sealant that is non-biodegradable and requires a shorter setting time for the sealant to solidify.

SUMMARY OF THE INVENTION

The present invention provides a non-biodegradable endodontic sealant composition. The sealant composition comprises the reaction product of a first paste and a second paste. At least one of the first paste or the second paste comprises a biocompatible hydrophilic monomer comprising unmodified 2-hydroxyethyl methacrylate. At least one of the first paste or the second paste comprises bioglass. The first paste comprises a first polymerizing agent and the second paste comprises a second polymerizing agent. The biocompatible hydrophilic monomer comprises unmodified 2-hydroxyethyl methacrylate (also known as "HEMA").

The present invention further provides a method for making the non-biodegradable sealant composition, which comprises preparing the first paste and second paste and combining the two pastes together. The two pastes are combined under conditions to achieve a polymerization reaction. The polymerization reaction is initiated by a reaction between the first polymerizing agent and the second polymerizing agent. In a preferred embodiment, the combining step further comprises conditions to achieve a setting time that is in a range of about 1 minute to about 1 hour.

The present invention further provides a method for treating humans having an affected area of tooth root, comprising administering the sealant composition to the affected area. The non-biodegradable sealant composition is preferably administered to an area where tissue, tooth, or bone are not intended to re-grow.

DETAILED DESCRIPTION OF THE INVENTION

The present invention is directed to a non-biodegradable endodontic sealant composition; a method for making the sealant composition; and a method for treating humans having an affected area of tooth root. The sealant composition comprises the reaction product of a first paste and a second paste. At least one of the first paste or the second paste comprises a biocompatible hydrophilic monomer. At least one of the first paste or the second paste comprises bioglass. The first paste comprises a first polymerizing agent and the second paste comprises a second polymerizing agent.

As used herein, the biocompatible hydrophilic monomer comprises unmodified 2-hydroxyethyl methacrylate (also known as "HEMA"). As used herein, the term "unmodified" means that additional substituents, such as, for example, degradable substitutents, are not bonded to the HEMA. The bioglass comprises calcium-based glass. The bioglass may include, for example, at least one of silicon dioxide, calcium oxide, sodium oxide, phosphorus pentoxide, calcium silicate, barium sulfate, aluminum oxide, or a combination thereof. Preferably, the bioglass comprises silicon dioxide, calcium oxide, and phosphorus pentoxide. The first polymerizing agent of the first paste preferably comprises an initiator and the second polymerizing agent of the second paste preferably comprises an accelerator. Most preferably, the initiator comprises benzoyl peroxide, and the accelerator comprises at least one of p-toluidine, p-toluenesulfinate, or a combination thereof.

In a preferred embodiment, the first paste comprises a biocompatible hydrophilic monomer, bioglass, and a first polymerizing agent; and the second paste comprises a biocompatible hydrophilic monomer, bioglass, and a second polymerizing agent. In alternative embodiments, the only constituents that are provided in separate pastes are the first polymerizing agent and the second polymerizing agent (e.g., the first paste comprises a biocompatible hydrophilic monomer, bioglass, and a first polymerizing agent; and the second paste comprises a second polymerizing agent). In other alternative embodiments, the first paste comprises a first polymerizing agent and any of a biocompatible hydrophilic monomer, and/or bioglass; and the second paste comprises a second polymerizing agent and any of a biocompatible hydrophilic monomer, and/or bioglass.

In a preferred embodiment, at least one of the first paste and second paste further comprises at least one antioxidant. One of the benefits of the antioxidant is that it reduces any toxicity of the sealant, such as any cytotoxicity of HEMA. The antioxidant may include, for example, at least one of ascorbic acid, glutathione, alpha-tocopherol, or a combination thereof, and most preferably comprises ascorbic acid.

The sealant composition may also comprise additional constituents which adjust the viscosity of the composition. For example, in an alternative embodiment, at least one of the first paste or the second paste comprises at least one polymerizable dimethacrylate monomer (e.g., triethylene glycol dimethacrylate). One benefit of dimethacrylates is that they may be used to increase or decrease the viscosity of the sealant composition. The desired viscosity depends on the particular use of the composition and can readily be determined by an artisan.

The sealant composition may also comprise additional constituents which adjust the radiopacity of the sealant, so that the sealant can be made visible by x-rays or other types of radiologic imaging systems. For example, in an alternative embodiment, at least one of the first paste or the second paste may comprise triphenylbismuth carbonate, which renders the sealant composition radiopaque.

The present invention also provides a method for making the non-biodegradable sealant composition, which comprises preparing the first paste and second paste and combining the two pastes together. The two pastes are combined under conditions to achieve a polymerization reaction which is initiated by a reaction between the first polymerizing agent and the second polymerizing agent. The polymerization reaction preferably comprises a free radical initiated addition polymerization. The first paste, second paste, and reaction product of the two pastes may have wide ranges of viscosities, depending on the amounts and types of constituents that are used.

In a preferred embodiment, the combining step comprises conditions which achieve a setting time that is in a range of about 1 minute to about 1 hour. The setting time can be varied by varying the reactants used in the composition. As used herein, "setting time" refers to the amount of time measured from the time that the two pastes are combined to the time that the reaction product of the combined pastes becomes solidified. The preferred setting time of about 1 minute to about 1 hour is substantially shorter than the setting time of prior art systems. A shorter setting time provides added convenience and comfort to a patient, as the patient does not have to wait as long for the composition to solidify and likely does not have to have any additional procedure performed before the composition solidifies. In a preferred embodiment, adding moisture to the composition is not required in order for the composition to set.

The present invention also provides a method for treating humans having a voided region into which no re-growth will occur, comprising administering the sealant composition to the voided region. The preferred use of the sealant composition is to seal portions of dental roots, preferably for root canal treatment. There are many clinical applications for the sealant composition in both endodontic and pedodontic practice, including, for example, sealing of perforations, furcation repair, pulp capping, apexification, repairing root that is damaged during a root canal procedure, and treating root resorption. The sealant composition may also be used as retrograde filling materials or pulpotomy agents.

The sealant composition of the present invention is preferably administered to an area where tissue, tooth, or bone are not intended to re-grow. The sealant composition is non-biodegradable, which makes it especially suitable for applications where the sealant is intended to provide a lasting seal and not be re-absorbed by the body. Non-biodegradability helps to ensure that the affected area remains sealed off from surrounding tissue, tooth, and bone. One of the advantages of non-biodegradability, for example, is that bacteria and other infectious organisms are prevented from migrating into the root canal cavity or from the root canal into bone.

EXAMPLES

Exemplary compositions according to the present invention are shown in the following examples. The amounts listed below were used in the particular compositions set forth in the Examples, but those amounts may vary over a range, as an artisan would readily recognize.

Example 1

According to a first exemplary embodiment, the Powder Composition (modified from Bioglass) included the components listed in Table 1.

TABLE 1

| Component | Weight % |
| --- | --- |
| Silica ($SiO_2$) | 35% |
| Sodium Oxide ($Na_2O$) | 24.5% |
| Calcium oxide (CaO) | 24.5% |
| Phosphorus Pento-oxide ($P_2O_5$) | 6.0% |
| Triphenylbismuth carbonate (($C_6H_5)_3BiCO_3$) | 10.0% |

Paste 1 and Paste 2 included the following components:
Paste 1: 5 ml HEMA+0.05 g Benzoyl Peroxide
Paste 2: 5 ml HEMA+0.05 ml N N dimethyl-p-Toluidine
Paste 1, Paste 2, and the Powder Composition of Table 1 were combined in the following amounts: 100 microliters (ul) of Paste 1+100 ul of Paste 2+0.312 g of Powder Composition. The setting time was 4 minutes.

Example 2

According to a second exemplary embodiment, the Powder Composition (modified from Bioglass) included the same components as those listed in Table 1.
Paste 1 and Paste 2 included the following components:
Paste 1: 5 ml HEMA+0.04 g Benzoyl Peroxide
Paste 2: 5 ml HEMA+0.04 ml N N dimethyl-p-Toluidine
Paste 1, Paste 2, and the Powder Composition of Table 1 were combined in the following amounts: 100 ul Paste 1+100 ul Paste 2+0.67 g Powder Composition. The setting time was 6-7 minutes.

Example 3

According to a third exemplary embodiment, the Powder Composition (modified from Bioglass) included the same components as those listed in Table 1.
Paste 1 and Paste 2 included the following components:
Paste 1: 5 ml HEMA+0.03 g Benzoyl Peroxide
Paste 2: 5 ml HEMA+0.02 ml N N dimethyl-p-Toluidine+0.05 g toluenesulfinate
Paste 1, Paste 2, and the Powder Composition of Table 1 were combined in the following amounts: 100 ul Paste 1+100 ul Paste 2+0.67 g Powder Composition. The setting time was 3 minutes.

Although the invention is illustrated and described herein with reference to specific embodiments, the invention is not intended to be limited to the details shown. Rather, various modifications may be made in the details within the scope and range of equivalents of the claims and without departing from the invention.

What is claimed:
1. A sealant composition consisting essentially of:
a reaction product of a first paste and a second paste,
wherein at least one of the first paste or the second paste consists essentially of: a biocompatible hydrophilic monomer consisting of unmodified 2-hydroxyethyl methacrylate, bioglass, and, optionally, at least one of: (i) at least one antioxidant, (ii) triethylene glycol dimethacrylate, and (iii) at least one radiopaque constituent;
the first paste further consists essentially of a first polymerizing agent, and the second paste further consists essentially of a second polymerizing agent;
wherein the sealant composition is non-biodegradable.

2. The sealant composition according to claim 1, wherein the bioglass is selected from the group consisting of silicon dioxide, calcium oxide, sodium oxide, phosphorus pentoxide, calcium silicate, barium sulfate, aluminum oxide, and combinations thereof.

3. The sealant composition according to claim 1, wherein the bioglass comprises silicon dioxide, calcium oxide, phosphorus pentoxide, and aluminum oxide.

4. The sealant composition according to claim 1, wherein the at least one antioxidant is included and is selected from the group consisting of ascorbic acid, glutathione, alpha-tocopherol, and combinations thereof.

5. The sealant composition according to claim 1, wherein the first polymerizing agent is an initiator and the second polymerizing agent is an accelerator.

6. The sealant composition according to claim 5, wherein the initiator is benzoyl peroxide and the accelerator is at least one of p-toluidine, p-toluensulfinate, or a combination thereof.

7. A method for making a sealant composition comprising:
preparing a first paste and a second paste,
wherein at least one of the first paste or the second paste consists essentially of: a biocompatible hydrophilic monomer consisting of unmodified 2-hydroxyethyl methacrylate, bioglass, and, optionally, at least one of: (i) at least one antioxidant, (ii) triethylene glycol dimethacrylate, and (iii) at least one radiopaque constituent;
the first paste further consists essentially of a first polymerizing agent, and the second paste further consists essentially of a second polymerizing agent; and
combining the first paste and the second paste under conditions to achieve a polymerization reaction, the polymerization reaction occurring upon combining the first paste and the second paste,
wherein the polymerization reaction is initiated by a reaction between the first polymerizing agent and the second polymerizing agent, and
wherein the sealant composition is non-biodegradable.

8. The method according to claim 7, wherein the bioglass is selected from the group consisting of silicon dioxide, calcium oxide, sodium oxide, phosphorus pentoxide, calcium silicate, barium sulfate, aluminum oxide, and combinations thereof.

9. The method according to claim 7, wherein the bioglass comprises silicon dioxide, calcium oxide, phosphorus pentoxide, and aluminum oxide.

10. The method according to claim 7, wherein the at least one antioxidant is selected from the group consisting of ascorbic acid, glutathione, alpha-tocopherol, and combinations thereof.

11. The method according to claim 7, wherein the first polymerizing agent is an initiator and the second polymerizing agent is an accelerator.

12. The method according to claim 11, wherein the initiator is benzoyl peroxide and the accelerator is at least one of p-toluidine, p-toluensulfinate, or a combination thereof.

13. The method according to claim 7, wherein the polymerization reaction comprises a free radical initiated addition polymerization.

14. The method according to claim 7, wherein the combining step comprises conditions to achieve a setting time, wherein the setting time is in a range of about 1 minute to about 1 hour.

15. A method for treating humans having a voided region into which no re-growth will occur, comprising the steps of:
administering to the voided region a sealant composition consisting essentially of a reaction product of a first paste and a second paste,
wherein at least one of the first paste or the second paste consists essentially of: a biocompatible hydrophilic monomer consisting of unmodified 2-hydroxyethyl methacrylate, bioglass, and, optionally, at least one of: (i) at least one antioxidant, (ii) triethylene glycol dimethacrylate, and (iii) at least one radiopaque constituent;
the first paste further consists essentially of a first polymerizing agent, and the second paste further consists essentially of a second polymerizing agent;
wherein the sealant composition is non-biodegradable.

16. The method according to claim 15, wherein the bioglass is selected from the group consisting of silicon dioxide, calcium oxide, sodium oxide, phosphorus pentoxide, calcium silicate, barium sulfate, aluminum oxide, and combinations thereof.

17. The method according to claim 15, wherein the bioglass comprises silicon dioxide, calcium oxide, aluminum oxide, and phosphorus pentoxide.

18. The method according to claim 15, wherein the at least one antioxidant is selected from the group consisting of ascorbic acid, glutathione, alpha-tocopherol, and combinations thereof.

19. The method according to claim 15, wherein the first polymerizing agent comprises is an initiator and the second polymerizing agent is an accelerator.

20. The method according to claim 19, wherein the initiator is benzoyl peroxide and the accelerator is p-toluidine, p-toluensulfinate, or a combination thereof.

21. The sealant composition according to claim 1, wherein the radiopaque constituent is triphenylbismuth carbonate.

22. The method according to claim 7, wherein the radiopaque constituent is triphenyl bismuth carbonate.

23. The sealant composition according to claim 15, wherein the radiopaque constituent is triphenylbismuth carbonate.

24. The sealant composition according to claim 1, wherein the at least one antioxidant, the triethylene glycol dimethacrylate, and the at least one radiopaque constituent are included.

* * * * *